United States Patent [19]

Agostini et al.

[11] Patent Number: 5,314,890
[45] Date of Patent: May 24, 1994

[54] 1-7 DISUBSTITUTED XANTHINE DERIVATIVES HAVING ANTIASTHMATIC ACTIVITY, THEIR PHYSIOLOGICALLY ACCEPTABLE SALTS, PHARMACEUTICAL COMPOSITIONS CONTAINING THEM AND PROCESS FOR THEIR PREPARATION

[75] Inventors: Orenzo Agostini; Carla Bacciarelli, both of Florence; Graziano Bonacchi, Pistoia; Mauro Fedi, Sesto Fiorentino; Stefano Manzini, Florence, all of Italy

[73] Assignee: Malesci Istituto Farmacobiologico S.p.A., Florence, Italy

[21] Appl. No.: 949,507

[22] PCT Filed: May 23, 1991

[86] PCT No.: PCT/IT91/00045
§ 371 Date: Nov. 17, 1992
§ 102(e) Date: Nov. 17, 1992

[87] PCT Pub. No.: WO91/17993
PCT Pub. Date: Nov. 28, 1991

[30] Foreign Application Priority Data

May 24, 1990 [IT] Italy ................. 47999 A/90

[51] Int. Cl.$^5$ ................. A61K 31/52; C07D 473/08
[52] U.S. Cl. ........................ 514/263; 544/267
[58] Field of Search ............. 544/267; 514/265, 263

[56] References Cited

U.S. PATENT DOCUMENTS

| | | | |
|---|---|---|---|
| 2,785,163 | 3/1957 | Swidinsky et al. | 260/256.4 |
| 4,829,089 | 5/1989 | Medwid et al. | 564/370 |
| 4,833,146 | 5/1989 | Gebert et al. | 544/267 |
| 4,868,186 | 9/1989 | Franzone et al. | 544/267 |
| 5,082,845 | 1/1992 | Wolf et al. | 544/267 |

FOREIGN PATENT DOCUMENTS 0260127 3/1988 European Pat. Off. .

OTHER PUBLICATIONS

Mann, F. G., and J. W. G. Porter, "The Synthesis and Properties of 1:7-Dialkyl Xanthines", Journal of the Chemical Society (1945), pp. 751-760.
Mann et al., Jour. Chemical Soc. pp. 751-760.

*Primary Examiner*—Mukund J. Shah
*Assistant Examiner*—P. K. Sripada
*Attorney, Agent, or Firm*—Beveridge, DeGrandi, Weilacher & Young

[57] ABSTRACT

Xanthine derivatives having antiasthmatic activity are disclosed which have the following formula:

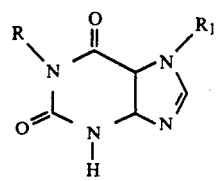

where R is a linear or branched alkyl chain group of from one to six carbon atoms, $R_1$ is a linear or branched alkyl or hydroxyalkyl group of from one to six carbon atoms. However, if R is methyl, then $R_1$ is not methyl, ethyl or propyl; if R is ethyl, then $R_1$ is not methyl or ethyl; and if R is methyl or n-butyl, then $R_1$ is not 2-hydroxypropyl. Also disclosed are pharmaceutical compositions containing such xanthine derivatives.

6 Claims, No Drawings

1-7 DISUBSTITUTED XANTHINE DERIVATIVES HAVING ANTIASTHMATIC ACTIVITY, THEIR PHYSIOLOGICALLY ACCEPTABLE SALTS, PHARMACEUTICAL COMPOSITIONS CONTAINING THEM AND PROCESS FOR THEIR PREPARATION

This invention relates to 1-7 disubstituted xanthine derivatives having antiasthmatic activity, as well as to their physiologically acceptable salts, to their pharmaceutical compositions and to the process for preparation therof.

It has been known for long time that substituted xanthines have bronchodilatory activity.

Indeed, theophylline (1,3-dimethyl-xanthine) is successfully employed since a long time for the treatment of bronchial asthma, though its efficacy is limited by side effects on the cardiovascular system and on the central nervous system (Goodman and Gilman's "The Pharmacological Basis of Therapeutics", MacMillan Publishing Company, 1985).

In more recent times, accurate investigations have been carried out for finding xanthine derivatives endowed with a higher activity and/or with a more selective action than theophylline. Accordingly many alkyl- or hydroxyalkyl-substituted derivatives in the 1, 3, 7 and 8 positions of the xanthine structure have been synthesized.

In all compounds which showed to be the most interesting as bronchodilatory compounds the position 3 always is alkyl-substituted (for instance, enprofylline; bamifylline; doxofylline; the Merck Index, 11th Edition, 1989) and in addition in a structure-activity study presented by Carl G. A. Persson (Carl G. A. Persson, Trends Pharmacol. Sci., 1982, 312-313) it is set forth that the $N_3$-alkyl substitution is essential for giving the xanthine structure its bronchodilatory activity.

Just few examples of $N_3$-unsubstituted xanthine derivatives exist in the scientific literature, and, on the other side, paraxanthine itself (1,7-dimethyl-xanthine) has been very little investigated as regards its pharmacological effects up to the present time (Aznan Lelo et al., J. Pharm. and Exp. Therapeutics 1989, 248, 315-319; M. J. Arnaud, C. Welsch in "Theophylline and other Methylxanthine" (The Proceedings of an International Symposium, Frankfurt/Main, May 29-30, 1981) Vieweg and Sohn Braunschweig R.F.T.), though it is the most important caffeine (1,3,7-trimethyl-xanthine) metabolite in man.

The properties and the synthesis of 1,7-dialkyl-xanthines have been disclosed in the literature by Frederick G. Mann et al. (Frederick G. Mann et al., J. Chem. Soc. 1945, 751-60), but the authors just limit themselves to report that such compounds have a remarkable antithyroid activity.

As regards their synthesis, the 1,7-dialkyl-substituted derivatives cannot be prepared through the well known Traube's procedure (W. Traube; Chem. Ber. 1900, 3035-3056) as modified by Papesch (V. Papesch and E. F. Schroeder; J. Org. Chem. 1951, 16, 1879-1890) starting from a monoalkyl-substituted urea, because 3-alkyl-xanthines are always obtained by means of such procedure, from which compounds the 3,7-dialkyl-xanthines are easily prepared through further alkylation.

The preparation through alkylation of 1-alkyl-xanthines gives, on the other side, a number of problems, because 1-alkyl-xanthines are difficult to synthesize (Mah. T. Schamin et al. J. Med. Chem. 1989, 32, 1231-1237) on the one hand, and on the other hand they would give through alkylation a mixture of 1,3- and 1,7-dialkyl-xanthines which cannot be easily separated.

In the article by Frederick G. Mann mentioned above some alternative synthesis are reported which are however very complicated and give very low yields.

Accordingly, it is possible to think reasonably that the limited development of 1,7-dialkyl-substituted xanthine derivatives is due both to the remarkable difficulties involved in synthesizing them and to the fact that the $N_3$-substituted derivatives have been considered up to the present time better compounds as regards their antibronchospastic activity.

The paraxanthine mentioned above also has never been deeply investigated as far as its pharmacological activity is concerned (Aznon Lelo et al., of the bibliographic references quoted herein). However, in laboratory tests carried out by the Applicant itself it was found that paraxanthine does not show any significant antibronchospastic activity.

On the contrary, it was surprisingly found according to the present invention that other 1,7-dialkyl- or 1-alkyl-7-hydroxy-alkyl-substituted xanthine derivatives show a significant bronchodilatory activity which is associated with reduced central exciting effects so that such compounds can be efficiently employed as antiasthmatic drugs.

Accordingly, the specific object of the present invention consists in xanthine derivatives having antiasthmatic activity of the general formula (I):

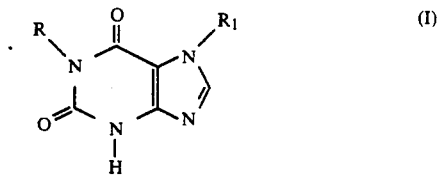

wherein:

R is a linear or branched alkyl chain of from one to six carbon atoms, and $R_1$ is a linear or branched alkyl or hydroxyalkyl chain group of from one to six carbon atoms, provided that $R_1$ is not methyl, or ethyl, or propyl when R is methyl; $R_1$ is not methyl or ethyl when R is ethyl; $R_1$ is not 2-hydroxy-propyl when R is methyl or n-butyl.

In the case wherein the R and/or $R_1$ substituting groups have an asymmetric carbon atom, this invention includes all possible optically active forms as well as the racemic mixtures of the compounds of the formula (I).

Moreover, the object of the present invention also consists in the physiologically acceptable salts of the xanthine derivatives of the formula (I), which also can be employed in the treatment of asthmatic diseases.

The pharmaceutical compositions containing the xanthine derivatives mentioned above or their physiologically acceptable salts also belong to the scope of the invention; such compositions being suitable for oral, rectal, parenteral, inhalation administration as well as for topical use, and useful for treatment of bronchial asthma, and being conveniently formulated as tablets, vials, syrups, drops, aerosols, suppositories, gels, ointments, sustained-release forms and so on.

Obviously, the compounds which are structurally different from those of the formula (I) but once administered to living organisms are transformed into compounds of the formula I and as such they exert their pharmacological effects are to be considered as included in the present invention.

Moreover, this invention relates to a procedure for the preparation of compounds of the formula I, wherein:

a) 6-amino-1-benzyl-5-bromo-2,4(1H)-pyrimidinedione (2) is reacted in N,N-dimethylformamide with an alkyl- or hydroxyalkylprimary amine of the formula $R_1NH_2$, wherein $R_1$ has the same meaning as that defined with reference to the compounds of the formula I;

b) the 6-amino-5-alkylamino-1-benzyl-2,4-(1H,3H)-pyrimidinediones obtained (3) are formylated preferably at 90° C. with formic acid, preferably of 98% concentration;

c) the resulting N-formyl derivatives (4) are alkylated with dialkylsulfates in diluted NaOH or with alkyl halides in a suitable solvent, in particular in N,N-dimethylformamide by previously forming the salts with alkaline hydrides or hydroxides;

d) the 3-alkyl-6-amino-1-benzyl-5-(N-formyl-N-alkylamino) 2,4-(1H,3H)-pyrimidinediones (5) are debenzylated through catalytic hydrogenation at room pressure in the presence of Pd/C and in an ammonia-water-alcohol solvent mixture; and e) the 3-alkyl-6-amino-5-(N-formyl-N-alkyl-amino)-2,4-(1H,3H)-pyrimidinediones so obtained (6) are finally subjected to cyclization with phosphorus oxychloride and N,N-dimethyl-formamide at 50°-60° C.

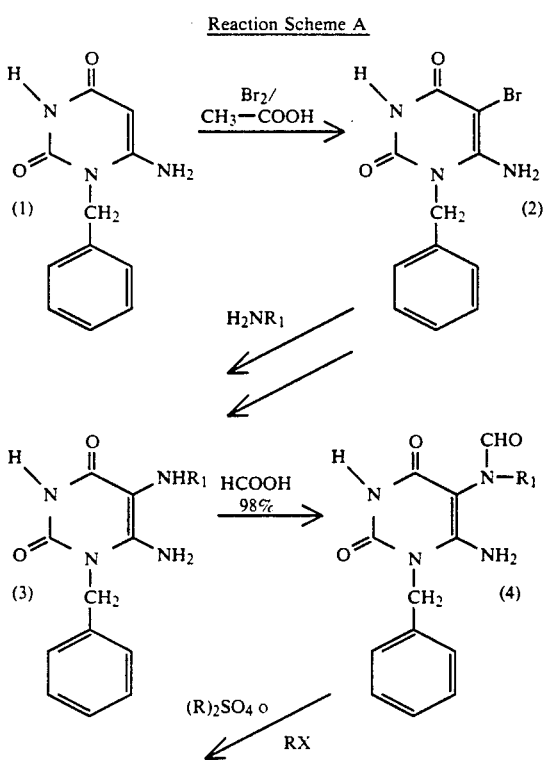

Reaction Scheme A

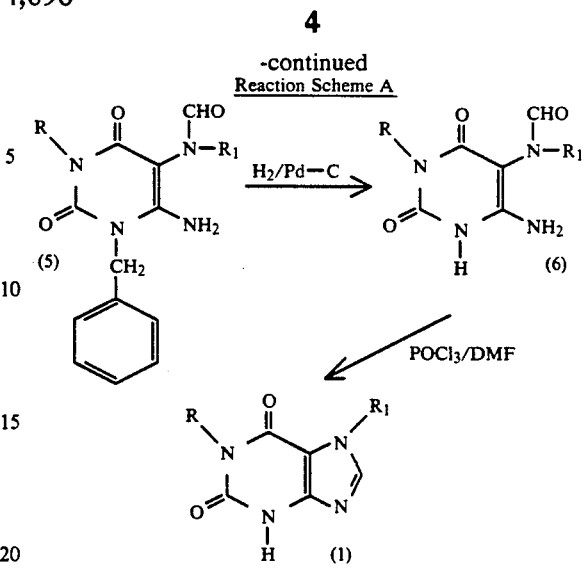

-continued
Reaction Scheme A

In the preparation process illustrated in the reaction scheme A the procedure by which W. Hutzenlaub and W. Pfleiderer (Liebigs Ann. Chem. 1979, 1847–1854) have synthesized paraxanthine is employed.

The reaction between 6-amino-1-benzyl-5-bromo-2,4(1H,3H)-pyrimidinedione (2) and primary alkylamines at 100° C. in N,N-dimethylformamide yields 6-amino-5-alkylamino-1-benzyl-2,4(1H, 3H)-pyrimidinediones (3) which are formylated at 90° C. with 98% formic acid (4) and then they are alkylated with dialkylsulfates in diluted NaOH or with alkyl halides in N,N-dimethylformamide by previously forming the salts with alkaline hydrides or hydroxides so as to yield 3-alkyl-6-amino-1-benzyl-5-(N-formyl-N-alkylamino)-2,4(1H, 3H)-pyrimidinediones (5).

At that point the process goes on through the debenzylation reaction which is carried out by catalytic hydrogenation at room pressure in the presence of Pd/C and in ammonia-water-alcohol solvent mixture for obtaining 3-alkyl-6-amino-5-(N-formyl-N-alkyl-amino)-2,4(1H, 3H)-pyrimidinediones (6) which are finally cyclized with phosphorus oxychloride and N,N-dimethylformamide so as to yield 1,7-dialkyl-xanthines of the general formula (I).

A second process is described according to the present invention for the preparation of compounds of the formula (I) as follows:

a) 1-alkyl-4-amino-2-methoxy-pyrimidine-6(1H)-ones (2) are nitrosated with the stoichiometric amount of sodium nitrite and hydrochloric acid, the reaction proceeding in dimethylsulfoxide at 60°-70° C.;

b) the 1-alkyl-4-amino-2-methoxy-5-nitroso-pyrimidine-6(1H)-ones so obtained (3) are preferentially reduced through catalytic hydrogenation under pressure (3–5 atm.) in an alcohol suspension and in the presence of $PtO_2$;

c) the 1-alkyl-4,5-diamino derivatives obtained (4) are cyclized by heating under reflux with 98% formic acid or by treatment at 100° C. with acetic anhydride and triethylorthoformiate;

d) the 1-alkyl-2-methoxy-hypoxanthines so obtained (5) are subsequently alkylated with dialkylsulfates in diluted NaOH or with alkyl halides in a suitable solvent, in particular N,N-dimethyl-formamide by previously forming the salts with alkaline hydrides or hydroxides or with alkyl epoxides in an alcohol environment and in the presence of pyridine;

e) the 1-alkyl-2-methoxy-7-alkyl-hypoxanthines (7) obtained after separation of the same from the corresponding 9-substituted isomers, which can be formed in the reaction corresponding to the step d), are finally treated in the cold with concentrated hydrochloric acid.

amount of water and then by adding the stoichiometric amount of concentrated HCl.

Moreover, 1-alkyl-4,5-diamino-2-methoxy-pyrimidine-6-(1H)-ones (4) are preferentially obtained by catalytic hydrogenation under pressure (3-5 atm.) of the corresponding nitroso derivatives in an alcohol suspen-

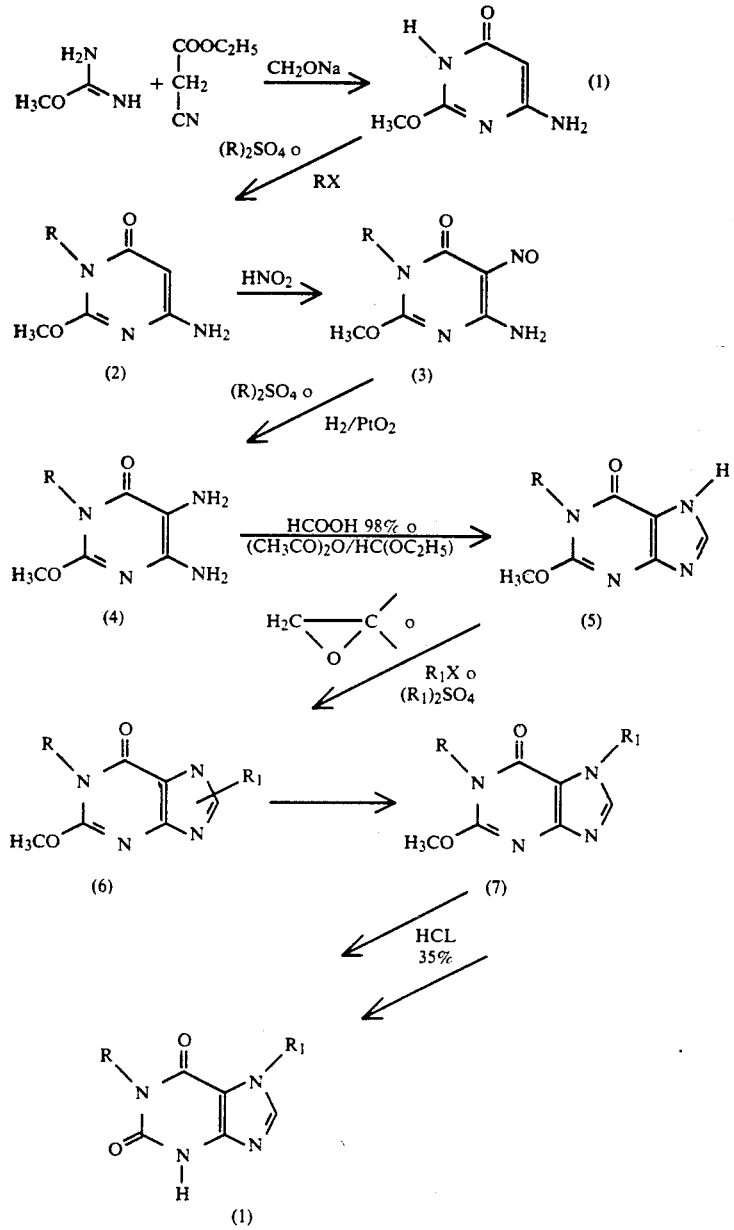

Reaction Scheme B sion and in the presence of $PtO_2$.

In the preparation process illustrated in the reaction scheme B, one proceeds in a way similar to the procedure of W. Pfleiderer (Chem. Ber. 1957, 90, 2272-2276) till obtaining 1-alkyl-4,5-diamino-2-methoxy-pyrimidine-6(1H)-ones (4). In the process as modified according to the present invention, 1-alkyl-4-amino-2-methoxy-5-nitroso-pyrimidine-6(1H)-ones (3) are preferentially obtained by reacting the corresponding 1-alkyl-4-amino-2-methoxy-pyrimidine-6(1H)-ones (2) at 60°-70° in dimethylsulfoxide with the stoichiometric amount of sodium nitrite dissolved in the minimum The cyclization reaction not performed according to W. Pfleiderer, can occur indifferently by heating under reflux with 98% formic acid or by treating at 100° C. with acetic anhydride and triethylorthoformate.

The 1-alkyl-2-methoxy-hypoxanthines (5) are subsequently alkylated by means of dialkylsulfate in diluted NaOH or with alkyl halides in N,N-dimethylformamide by previously forming the salt with alkaline hydrides or hydroxides, or with alkyl epoxides in alcohol as solvent and in the presence of pyridine.

In each instance, isomeric mixtures (6) of compounds alkylated in the 7 and 9 positions of the hypoxanthine structure can be obtained, said mixtures being separable through fractional crystallization or through preparative HPLC or through flash chromatography.

The 1-alkyl-2-methoxy-7-alkyl-hypoxanthines (7) are finally treated in the cold with concentrated HCl so as to yield the 1,7-dialkyl-xanthines of the general formula I.

The following examples of the preparation of the compounds of the present invention are intended for illustrating the invention itself in a non-limitative way.

PREPARATION OF 1-METHYL-7-ISOBUTYL-XANTHINE (Reaction Scheme A)

1. Preparation of 6-amino-5-isobutylamino-1-benzyl-2,4-(1H,3H)-pyrimidinedione.

To a suspension of 50 g (0.169 moles) of 6-amino-1-benzyl-5-bromo-2,4(1H,3H)-pyrimidinedione (W. Hutzenlaub; W. Pfleiderer, Liebigs Ann. Chem., 1979, 1847–1854) in 250 ml of N,N-dimethylformamide, 50 ml (0.5 moles) of isobutylamine is added dropwise with stirring. The solution so obtained is kept at 90°–100° C. for 3 hours; then the solution is allowed to cool till obtaining a large amount of a precipitate which is then filtered under vacuum and washed with ethyl alcohol and ether. 20 g of a white product is obtained. m.p. 209°–211° C.

A solid residue is obtained from the reaction solution after concentration to dryness, and said residue is taken up with water and filtered. So a further amount of 7 g of product is obtained. m.p. 204°–206° C.

2. Preparation of 6-amino-1-benzyl-5-(N-formyl-N-isobutylamino)-2,4(1H,3H)-pyrimidinedione.

A solution of 20 g (0.069 moles) of 6-amino-5-isobutylamino-1-benzyl-2,4(1H,3H)-pyrimidinedione in 80 ml of 98% formic acid is heated up to 90° C. for 45 minutes, and subsequently it is evaporated to dryness in vacuo. The solid so obtained is taken up with ethyl alcohol, filtered in vacuo and washed with ether. m.p. 255°–258° C. Yield 20 g.

3. Preparation of 6-amino-1-benzyl-3-methyl-5-(N-formyl-N-isobutylamino)-2,4(1H,3H)-pyrimidinedione.

To a solution of 7 g (0.022 moles) of 6-amino-1-benzyl-5-(N-formyl-N-isobutylamino)-2,4(1H,3H)-pyrimidinedione in 45 ml of 0.7M NaOH, 3.2 ml of dimethylsulfate is added dropwise. After a few minutes a precipitate begins to form, which is filtered in vacuo and washed with water. Yield: 4.5 g. m.p. 174°–5° C.

4. Preparation of 6-amino-3-methyl-5-(N-formyl-N-isobutylamino)-2,4(1H,3H)-pyrimidinedione.

A suspension of 2.5 g (7.7 moles) of 6-amino-1-benzyl-3-methyl-5-(N-formyl-N-isobutylamino)-2,4(1H,3H)-pyrimidinedione in 70 ml of methyl alcohol is hydrogenated at room pressure with stirring in the presence of 10 mg of 10% Pd/C. The stoichiometric amount of hydrogen is absorbed in about 3 hours, then the suspension is filtered, the solution so obtained is evaporated to dryness and the solid residue is taken up with ethyl alcohol, filtered in vacuo and washed with ether. Yield 1.5 g. m.p. above 300° C.

5. Preparation of 1-methyl-7-isobutyl-xanthine.

To a suspension of 1 g (4.2 mmoles) of 6-amino-3-methyl-5-(N-formyl-N-isobutylamino)-2,4-(1H,3H)-pyrimidinedione in 5 ml of N,N-dimethylformamide 0,6 ml of a solution prepared by adding 0,9 ml of phosphorous oxychloride to 1 ml of N,N-dimethylformamide is added. After heating at 60° C. for 30 minutes, the solution so obtained is evaporated to dryness in vacuo and the semisolid residue is taken up with ice water. The solid so obtained is filtered in vacuo, washed with water and dried in an oven at 80°–100° C. Yield: 800 mg. m.p. 222° C. ($H_2O$).

Elemental analysis ($C_{10}H_{14}N_4O_2$): $C_{calcd}$ 54.04; $C_{found}$ 53.98. $H_{calcd}$ 6.35; $H_{found}$ 6.36. $N_{calcd}$ 25.21; $N_{found}$ 25.25.

PREPARATION OF 1-METHYL-7-(2-METHYL-2-HYDROXY-PROPYL)-XANTHINE (Reaction Scheme)

1. Preparation of 1-methyl-4-amino-5-nitroso-2-methoxy-pyrimidine-6(1H)-one.

To a solution of 60 g (0.39 moles) of 1-methyl-4-amino-2-methoxy-pyrimidine-6(1H)-one (W. Pfleiderer, Chem. Ber. 1957, 90, 2272–2276) in 900 ml of dimethylsulfoxide, 28.5 g (0.41 mmoles) of sodium nitrite dissolved in 60 ml of water is added at 60° C. with vigorous stirring, and next 34 ml of 35% HCl is added dropwise. After a few minutes, a precipitate of blue colour is formed. The solution is allowed to cool in about 1.5 hours to room temperature, then 2 l of water is added with stirring and after 1.5 hours the violet precipitate is filtered off in vacuo and washed with water, ethyl alcohol and ether. Yield 65 g. m.p. 125°–126° C. (dec.). Elemental analysis ($C_6H_8N_4O_3$, $H_2O$) C, H, N.

2. Preparation of 1-methyl-4,5-diamino-2-methoxy-pyrimidine-6(1H)-one.

A suspension of 20.2 g (0.1 moles) of 1-methyl-4-amino-5-nitroso-2-methoxy-pyrimidine-6(1H)-one in 600 ml of méthyl alcohol is hydrogenated under pressure (3 atm.) and with stirring in the presence of 50 mg of $PtO_2$. The reaction is over after about 1.5 hours and the solution so obtained is filtered and evaporated to dryness. The solid residue is crystallized from 120 ml of water, so that 13 g of a yellow crystalline compound is obtained, which is dried in vacuo on $P_2O_5$ and after drying melts at 162°–163° C. Elemental analysis ($C_6H_{10}N_4O_2$) C, H, N.

3. Preparation of 1-methyl-2-methoxy-hypoxanthine.

A suspension of 13 g (0.76 moles) of 1-methyl-4,5-diamino-2-methoxy-pyrimidine-6(1H)-one in 100 ml of acetic anhydride and 100 ml of triethylorthoformate is stirred for 2 hours at room temperature and then it is heated at 120° C. for 3 hours. The solution so obtained is evaporated to dryness, the residue is taken up with ether, filtered in vacuo and crystallized from 100 ml of water. Thus 7.5 g of a compound with m.p. 230°–240° C. is obtained. Elemental analysis ($C_7H_8N_4O_2$) C, H, N.

4. Preparation of 1-methyl-2-methoxy-7-(2-methyl-2-hydroxy-propyl)-hypoxanthine.

To a suspension of 7.2 g (0.04 moles) of 1-methyl-2-methoxy-hypoxanthine in 100 ml of methyl alcohol, 0.6 ml of pyridine and 6 ml of 1,2-epoxy-2-methyl-propane (J. Am. Chem. Soc., 77, 1955, 5083; J. Am. Chem. Soc. 58, 1936, 2396–2402) are added. The suspension is refluxed for 3 hours and a complete dissolution occurs. The solution is evaporated to dryness and the residue is dissolved by heating with 70 ml of isopropyl alcohol. After a long period of standing, 4 g of a compound with m.p. 180° C. precipitates. Elemental analysis ($C_{11}H_{16}N_4O_3$) C, H, N.

5. Preparation of 1-methyl-7-(2-methyl-2-hydroxy-propyl)-xanthine.

A solution of 4 g (0.016 moles) of 1-methyl-2-methoxy-7-(2-methyl-2-hydroxy-propyl)-hypoxanthine in 30 ml of concentrated HCl is kept at room temperature for 30 hours, then it is concentrated to dryness under vacuum and the solid residue is crystallized from 30 ml of $H_2O$.

Yield 3 g; m.p. 265° C. ($H_2O$)

Elemental analysis ($C_{10}H_{14}N_4O_3$): $C_{calcd}$. 50.41; $C_{found}$ 50.46. $H_{calcd}$. 5.92; $H_{found}$ 6.08. $N_{calcd}$. 23.52; $N_{found}$ 23.62.

In the following the pharmacological tests carried out with the compounds according to the present invention are reported, such tests being referred to similar tests performed with theophylline and, in a few cases, with paraxanthine.

Acute toxicity

Starved (18 h) male Swiss mice (20 g weight) received drugs orally (0.2 ml/10 g weight).

Mice were observed for 10 days after drug administration. Death and symptoms were evaluated $LD_{50}$ was obtained according to Litchfield and Wilcoxon (J. Pharm. Expt. Ther. 96, 99, 1949).

| DRUG | $LD_{50}$ mg/kg |
| --- | --- |
| 1-methyl-7-Isobutyl-xanthine | 303 |
| Theophylline | 230 |

"In vitro" antibronchospastic activity

Antibronchospastic effect was assessed in isolated guinea pig bronchi (Manzini et al. Br. J. Pharmacol. 98, 1077; 1989). A steady tonic bronchomotor response was produced by administration of carbachol (0.3 μM) or capsaicin (0.3 μM, in presence of thiorphan 10 μM) on which a concentration-response curve with the various xanthine derivatives was carried out. In table 1 are shown their potencies expressed as $IC_{50}$.

TABLE 1

| Antibronchospastic activity in isolated guinea pig bronchi. Results are expressed as $IC_{50}$ μM (95% C.L.) | | | |
| --- | --- | --- | --- |
| | n | Carbachol | Capsaicin |
| Theophylline | (5) | 92 (69–139) | 40 (34–47) |
| 1-methyl-7-isobutyl-xanthine | (8) | 31 (29–34) | 21 (19–23) |
| Paraxanthine | (3) | 135 (94–241) | 82 (68–102) |

Antagonism toward acetylcholine- and capsaicin-induced bronchomotor effects in anaesthetized guinea-pig Anaesthetized guinea-pig were used D-Tubocurarine (3 mg/kg i.v.) was administered, and a mechanic ventilation (60 strokes/min) with a pump through a tracheal cannula was carried out Drugs were administered intravenously in a volume less than 0.5 ml/kg through a jugular cannula. Acetylcholine (25 μg/kg) or capsaicin (2.5 μg/kg) administration evoked a powerful and transient increase in tracheal insufflation pressure which was repeatable after 30 min. Testing xanthine derivative (70 μmol/kg i.v.) was administered 15 min before the second challenge with the agonist. Antibronchospastic activity was expressed as inhibition percentage referred to the first increase of tracheal insufflation pressure. Data are shown in Table 2.

TABLE 2/1

Inhibitory effect of i.v. administered xanthines on acetylcholine (Ach), capsaicin (Caps) induced bronchospasm in anaesthetized guinea pigs.
Xanthines were administered at doses of 70 μmol/Kg.
Values are expressed as inhibition percentage towards control responses (means ± s.e.m.). In brackets are reported number of experiments.

| | Ach | Caps |
| --- | --- | --- |
| 1-methyl-7-isobutyl xanthine | 54 ± 5 (5) | 52 ± 3 (5) |
| Theophylline | 51 ± 8 (9) | 51 ± 7 (8) |
| Paraxanthine | N.D. | N.D. |

N.D.—not determined
N.A.—not active

Antagonism toward ovoalbumin induced bronchomotor effects in anaesthetized guinea pigs.

Anaesthetized guinea pigs (sensitized with 100 mg/Kg s.c. plus 100 mg/Kg i.p. of ovoalbumin (OA) 14 days before tests) were used as described previously although bronchospasm was produced by OA intratracheal aerosol administration (0.5% for 20 s.). Testing substances (140 μmol/Kg i.v.) were administered 15 min. before.

Antibronchospastic activity was expressed as changes in pulmonary insufflation pressure (KPa) after OA aerosol administration and as inhibition percentage referred to control group. Data are shown in Table 2/2.

TABLE 2/2

| | n | KPa | % inhibition |
| --- | --- | --- | --- |
| Controls | 20 | 1.80 ± 0.15 | — |
| 1-methyl-7-isobutyl xanthine | 5 | 0.25 ± 0.08 | 86 |
| Theophylline | 5 | 0.45 ± 0.04 | 75 |
| Paraxanthine | | | N.A. |
| 1-methyl-7-(2-methyl-2-hydroxy)propyl-xanthine | 8 | 1.15 ± 0.15 | 36 |

Antagonism toward antigen-induced bronchospasm in sensitized guinea-pigs

Guinea-pigs (sensitized with 100 mg/kg s.c. plus 100 mg/kg i.p. of ovalbumin 14 days before) (Herxheimer and Streseman-Arch. Int. Pharmacodyn. Ther. 125, 265; 1960) were challenged by an aerosol of 0.5% ovalbumin, for a period of 10 sec. in a closed chamber.

In a first set of experiments, number of aerosol-induced bronchospasms was registered in control conditions or 1 hr after the oral administration of testing substances. Data are reported in Table 3.

TABLE 3

"In vivo" antibronchospastic activity of xanthines administered orally (0.55 mmol/kg) to sensitized guinea-pigs, 1 hour before exposure to an aerosol with ovalbumin.
Data (mean ± s.e.m.) are expressed as number of bronchospasms recorded in 5 minutes.

| | n | bronchospasm/min |
| --- | --- | --- |
| Control group | 12 | 8.4 ± 0.8 |
| 1-methyl-7-isobutyl-xanthine | 9 | 5.0 ± 1.1* |
| Theophylline | 6 | 4.6 ± 1.2* |

*$p < 0.05$

Effects on central nervous system

Pentylentetrazol-induced letality in mice

Starved (20 h) male Swiss mice (20 g body weight) received i.p. pentylentetrazol (PTZ) in a convulsive dose which produced death in about 10% of animals (60–75 mg/kg). Mice were observed for 1 h after PTZ injection. The drugs were administered orally (0.55 mmol/kg) in a volume of 20 ml/kg 1 h before PTZ. CNS excitation was valued as increase of PTZ mortality. Results are shown in Table 4.

Chloriazepoxide-induced sleep in mice

Starved (20 h) male Swiss mice (20 g body weight) were injected with chlordiazepoxide (CDO) (100 mg/kg i.p.) and the duration of the induced sleep assessed. Sleeping time was defined as the time elapsing from the loss to the recovery of the righting reflex. The drugs were administered orally (0.55 mmol/kg) in a volume of 20 ml/kg 1 h before CDO. CNS excitation was valued as decrease in sleeping time (Table 4).

Chlordiazepoxide-induced sleep in mice

Starved (20 h) male Swiss mice (20 g body weight) were injected with chlordiazepoxide (CDO) (100 mg/kg i.p.) and the duration of the induced sleep assessed. Sleeping time was defined as the time elapsing from the loss to the recovery of the righting reflex. The drugs were administered orally (0.55 mmol/kg) in a volume of 20 ml/kg 1 h before CDO. CNS excitation was valued as decrease in sleeping time (Table 4).

TABLE 4

Effect of orally (0.55 mM/kg) administered xanthine derivatives on pentylentetrazol (PTZ)-induced mortality and chlordiazepoxide (CDO)-induced sleep in mice

|  | PTZ test mortality rate (%) | CDO test sleeping-time (min) |
| --- | --- | --- |
| Controls | 10 | 27.1 ± 3.5 |
| Theophylline | 80 | 7.8 ± 2.2* |
| 1-methyl-7-isobutyl xanthine | 20 | 26.1 ± 3.3 |
| Paraxanthine | 82 | 2.3 ± 1.5* |
| 1-methyl-7-(2-methyl-2-hydroxy) propyl-xanthine | 0 | 64.2 ± 12.8 |

*p < 0.01

We claim:

1. Xanthine derivatives having antiasthmatic activity of the formula (I):

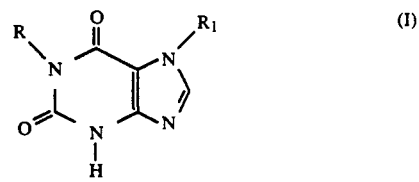

wherein
R is a linear or branched alkyl chain group of from one to six carbon atoms, and $R_1$ is a linear or branched alkyl or hydroxyalkyl group of from one to six carbon atoms, provided that $R_1$ is not methyl, or ethyl, or propyl when R is methyl; $R_1$ is not methyl or ethyl when R is ethyl; $R_1$ is not 2-hydroxy-propyl when R is methyl or n-butyl.

2. An optically active form and racemic mixture of the compound according to claim 1 where R and/or $R_1$ have an asymmetric carbon atom.

3. A physiologically acceptable salt of the xanthine derivative according to claim 1.

4. A pharmaceutical composition containing the xanthine derivative according to claim 1 or its physiologically acceptable salt and a pharmaceutically acceptable carrier, said composition being suitable for oral, rectal, parenteral, inhalation administration and for topical use and useful in the treatment of bronchial asthma.

5. The pharmaceutical composition according to claim 4 formulated in the form of tablets, vials, syrups, drops, aerosols, suppositories, gels, ointments, or sustained-release form.

6. A method of treating asthma comprising administering to a patient in need thereof an amount of the pharmaceutical composition according to claim 4 effective to treat asthma.

* * * * *